(12) United States Patent
Kim et al.

(10) Patent No.: US 9,540,644 B2
(45) Date of Patent: Jan. 10, 2017

(54) SMALL INTERFERENCE RNA FOR INHIBITING INTRACELLULAR EXPRESSION OF RIBOSOMAL PROTEIN S3

(71) Applicant: Korea University Research and Business Foundation, Seoul (KR)

(72) Inventors: Joon Kim, Seoul (KR); Hag Dong Kim, Gyeonggi-do (KR); Se Hyun Lee, Seoul (KR); Hee-Woong Yang, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/766,379

(22) PCT Filed: Feb. 7, 2014

(86) PCT No.: PCT/KR2014/001053
§ 371 (c)(1),
(2) Date: Aug. 6, 2015

(87) PCT Pub. No.: WO2014/123384
PCT Pub. Date: Aug. 14, 2014

(65) Prior Publication Data
US 2016/0046937 A1    Feb. 18, 2016

(30) Foreign Application Priority Data
Feb. 7, 2013    (KR) .................. 10-2013-0014075

(51) Int. Cl.
*A61K 48/00*    (2006.01)
*C12N 15/113*    (2010.01)

(52) U.S. Cl.
CPC ......... *C12N 15/113* (2013.01); *C12N 2310/14* (2013.01)

(58) Field of Classification Search
CPC .................................................. A61K 48/00
See application file for complete search history.

(56) References Cited

U.S. PATENT DOCUMENTS 7,820,809 B2 * 10/2010 Khvorova ............ A61K 31/713 435/6.1
2009/0258002 A1    10/2009 Barrett et al.

FOREIGN PATENT DOCUMENTS

| KR | 10-2003-0037856 A | 5/2003 |
| KR | 10-2010-0015529 A | 2/2010 |
| KR | 10-2010-0090341 A | 8/2010 |
| WO | 2008110624 A2 | 9/2008 |
| WO | 2008110624 A9 | 9/2008 |
| WO | 2008131426 A1 | 10/2008 |

OTHER PUBLICATIONS

Brummelkamp, T., et al., "A System for Stable Expression of Short Interfering RNAs in Mammalian Cells", Science, Apr. 19, 2002, pp. 550-553, vol. 296.
Demidov, V., "PNA and LNA throw light on DNA", Trends in Biotechnology, Jan. 2003, pp. 4-7, vol. 21, No. 1.
Dykxhoorn, D., et al., "Running Interference: Prospects and Obstacles to Using Small Interfering RNAs as Small Molecule Drugs", Annu. Rev. Biomed. Eng., Apr. 17, 2006, pp. 377-402, vol. 8.
Fire, A., et al., "Potent and specific genetic interference by double-stranded RNA in Caenorhabditis elegans", Nature, Feb. 19, 1998, pp. 806-811, vol. 391.
Hegde, V., et al., "Knockdown of ribosomal protein S3 protects human cells from genotoxic stress", DNA Repair, Oct. 17, 2006, pp. 94-99, vol. 6.
Karkare, S., et al., "Promising nucleic acid analogs and mimics: characteristic features and applications of PNA, LNA, and morpholino", Appl Microbiol Biotechnol, May 9, 2006, pp. 575-586, vol. 71.
Krueger, U., et al., "Insights into Effective RNAi Gained from Large-Scale siRNA Validation Screening", Oligonucleotides, Jun. 2007, pp. 237-250, vol. 17.
Paul, C., et al., "Effective expression of small interfering RNA in human cells", Nature Biotechnology, May 2002, pp. 505-508, vol. 29.
Pogue-Geile, K., et al., "Ribosomal Protein Genes Are Overexpressed in Colorectal Cancer: Isolation of a cDNA Clone Encoding the Human S3 Ribosomal Protein", Molecular and Cellular Biology, Aug. 1991, pp. 3842-3849, vol. 11, No. 8.
Veedu, R., et al., "Locked Nucleic Acids: Promising Nucleic Acid Analogs for Therapeutic Applications", Chemistry & Biodiversity, Mar. 15, 2010, pp. 536-542, vol. 7.
Wan, F., et al., "Ribosomal Protein S3: A KH Domain Subunit in NF-KB Complexes that Mediates Selective Gene Regulation", Cell, Nov. 30, 2007, pp. 927-939, vol. 131.
Graifer, D., et al, "Eukaryotic ribosomal protein S3: A constituent of translational machinery and an extraribosomal player in various cellular processes", "Biochimie", Nov. 13, 2013, pp. 8-18, vol. 99.
Ko, S., et al., "Human Ribosomal Protein S3 (hRpS3) Interacts with Uracil-DNA Glycosylase (hUNG) and Stimulates its Glycosylase Activity", "Mutation Research", Oct. 7, 2008, pp. 54-64, vol. 648.

* cited by examiner

*Primary Examiner* — Kimberly Chong
(74) *Attorney, Agent, or Firm* — Hultquist, PLLC; Steven J. Hultquist

(57) ABSTRACT

The present invention relates to a small interference RNA (siRNA) for specifically inhibiting the expression of ribosomal protein in cells, and more particularly, to an siRNA that specifically inhibits the expression of endogenous rpS3 protein in cells without influencing tagged overexpressed protein. The siRNAs of the present invention are excellent in terms of economy and efficiency compared to conventional commercially available products.

5 Claims, 2 Drawing Sheets

SMALL INTERFERENCE RNA FOR INHIBITING INTRACELLULAR EXPRESSION OF RIBOSOMAL PROTEIN S3

CROSS-REFERENCE TO RELATED APPLICATIONS

This application is a U.S. national phase under the provisions of 35 U.S.C. §371 of International Patent Application No. PCT/KR14/01053 filed Feb. 7, 2014, which in turn claims priority of Korean Patent Application No. 10-2013-0014075 filed Feb. 7, 2013. The disclosures of such international patent application and Korean priority patent application are hereby incorporated herein by reference in their respective entireties, for all purposes.

TECHNICAL FIELD

The present invention relates to an siRNA (small interference RNA) that can bind to a specific site of ribosomal protein in cells so as to specifically inhibit the expression of the ribosomal protein.

BACKGROUND ART

Proteins are involved in all physiological processes, from cell signaling to tissue remodeling to organ function. Thus, protein synthesis in cells is a very important process, and ribosomes perform this function. Ribosomes are cell organelles that connect amino acids to form proteins, and are large subunits composed of ribosomal proteins and ribosomal RNA.

rpS3 (ribosomal protein S3), a component of ribosomes, is located on the outer surface of the 40S subunit and is cross-linked to the initiation factor eIF2 and eIF3. As rpS3 has a nuclear localization of signal in the N-terminal region, it is believed that the translation functions of rpS3 operate in the cytosol, and the repair function operates in the nucleus. In addition to their role in ribosomal functions, many ribosomal proteins have secondary functions in replication, transcription, RNA processing, DNA repair, and malignant transformation.

The rpS3 gene is located on human chromosome 11q13.3-q13.5. Particularly, it was reported that the rpS3 gene is overexpressed in colorectal cancer patients. Thus, rpS3 gene products are overexpressed in colorectal cancer, and are highly likely to be associated with other cancers. In addition, studies on the region 11q13.3-q13.5 indicate that the structural abnormality and amplification of the gene often occur, and the gene is overexpressed upon the development of human cancers such as multiple endocrine neoplasia type I, breast carcinoma or B cell neoplasia (Pogue-Geile et al., *Mol. Cell. Biol.*, 11: 3842-3849, 1991).

As used herein, the term "siRNA (small interference RNA)" refers to a short double-strand RNA composed of about ten nucleotides to several tens of nucleotides, which induce RNAi (RNA interference). RNA interference ("RNAi") is a method of post-transcriptional inhibition of gene expression that is conserved throughout many eukaryotic organisms, and it refers to a phenomenon in which a double-stranded RNA composed of a sense RNA having a sequence homologous to the mRNA of the target gene and an antisense RNA having a sequence complementary thereto is introduced into cells or the like so that it can selectively induce the degradation of the mRNA of the target gene or can inhibit the expression of the target gene. RNAi is induced by a short (i.e., less than 30 nucleotides) double-stranded RNA ("dsRNA") molecule present in cells (Fire A. et al., *Nature,* 391: 806-811, 1998). Because RNAi can selectively inhibit the expression of the target gene as described above, it is attracting considerable attention as a simple gene knock-down method that acts as a substitute for a conventional gene destruction method based on inefficient homologous recombination. When siRNA is introduced into cells, the expression of the mRNA of the target gene having a nucleotide sequence complementary to that of the siRNA will be inhibited.]

The siRNA and the targeted mRNA bind to an RNA-induced silencing complex ("RISC"), which cleaves the targeted mRNA. The siRNA is apparently recycled much like a multiple-turnover enzyme, with 1 siRNA molecule capable of inducing cleavage of approximately 1000 mRNA molecules. Thus, siRNA-mediated RNAi degradation of an mRNA is more effective than currently available technologies for inhibiting expression of a target gene.

However, unlike the initial expectation that RNAi technology can be applied to the RNA of all genes to selectively inhibit the expression of the RNA, it has recently been found that the RNAi technology is not applied, because some genes are unknown in high-throughput RNAi screening procedures (Krueger et al., *Oligonucleotides,* 17:237-250, 2007). In addition, in past several years, algorithms for predicting siRNA sequences by statistical analysis based on databases have been developed. However, it is known that, because computational algorithms are not perfect, all siRNAs determined by an in silico method using the algorithm do not effectively inhibit the target mRNA in cells and in vivo, and the most efficient siRNA can be determined only by experimental verification (Derek et al., *Annu. Rev. Biomed. Eng.*, 8:377-402, 2006).

As described above, theoretically predicted siRNAs must not effectively inhibit the ability of mRNA, and highly efficient siRNA nucleotide sequences should be found to achieve therapeutic purposes. For this reason, it is very important to find a specific hyperactive target having high inhibitory effects on the target mRNA. In addition, it is required to identify the optimum sequence having an excellent expression inhibitory effect by preparing siRNAs based on a number of target sites selected per mRNA of a single gene and directly examining the effects of the siRNAs directly, at least at the cellular level.

Accordingly, the present inventors have made extensive efforts to develop an siRNA for inhibiting the expression of ribosomal protein S3 (rpS3), and as a result, have constructed an rpS3 siRNA that bind to the specific target site of rpS3, and have found that the constructed siRNA has an excellent effect of inhibiting the expression of endogenous rpS3 protein, compared to commercially available products, thereby completing the present invention.

DISCLOSURE OF INVENTION

It is an object of the present invention to provide an siRNA for specifically inhibiting the expression of rpS3.

To achieve the above object, the present invention provides an siRNA for inhibiting the expression of rpS3 protein, the siRNA binding to a nucleotide sequence corresponding to positions 777 to 795 or 796 to 814 of an rpS3 mRNA having a nucleotide sequence of SEQ ID NO: 1.

BEST MODE FOR CARRYING OUT THE INVENTION

Unless defined otherwise, all technical and scientific terms used herein have the same meaning as commonly understood by one of ordinary skills in the art to which the invention pertains. Generally, the nomenclature used herein and the experiment methods, which will be described below, are those well known and commonly employed in the art.

The present inventors have constructed an siRNA having an excellent effect of specifically inhibiting the expression of endogenous rpS3 protein in cells without influencing an overexpressed protein.

Figure 1:
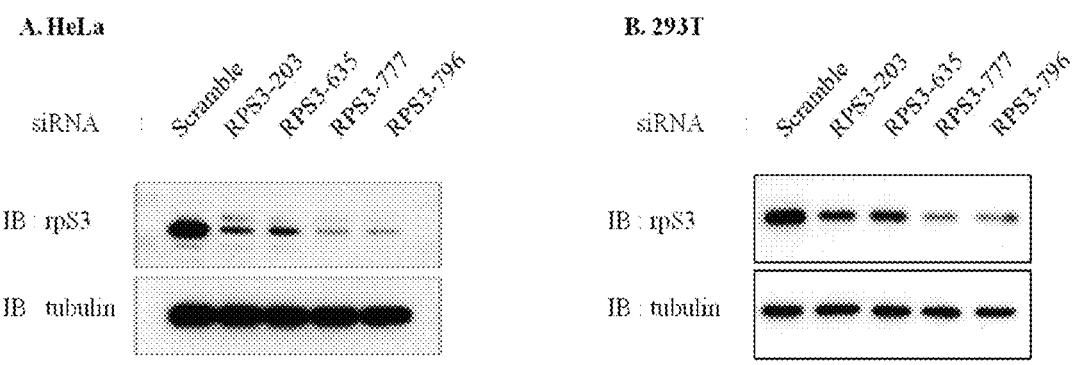
FIG. 1 shows the results of analyzing the efficiencies of rpS3 siRNAs introduced into cells (lane 1: scramble siRNA, lane 2: RPS3-203, lane 3: RPS3-635, lane 4: RPS3-777, and lane 5: RPS3-796).

In the present invention, in order to confirm whether the constructed rpS3 siRNA efficiently operates after intracellular introduction, each of scramble siRNA as a control, siRPS-203 constructed previously by the present inventors so as to target the rpS3 protein, and each of siRPS3-777 and 796 constructed in the present invention, was introduced into various animal cells, and the levels of the rpS3 protein in the cells were measured by Western blotting. As a result, it was found that the scramble siRNA used as a control showed no change in the level of the rpS3 protein in the cells, whereas the 777 and 796 siRNAs newly constructed in the present invention greatly inhibited the expression level of the rpS3 protein, and also significantly inhibited the expression level of the protein compared to the 203 and 635 siRNAs that have been used in the prior art (FIG. 1).

In other words, in an example of the present invention, it could be seen that siRPS3-777 and 796 specifically inhibited the expression level of the rpS3 protein.

Thus, in one aspect, the present invention is directed to an siRNA (SEQ ID NOs: 2 and 3) that inhibits the expression of rpS3 protein by its binding to a target nucleotide sequence selected from the group consisting of: a nucleotide sequence corresponding to positions 777 to 795 and 796 to 814 of an rpS3 mRNA having a nucleotide sequence of SEQ ID NO: 1.

The siRNA according to the present invention may have a length of 15-21 nucleotides.

As used herein, the term "siRNA" refers to a short double-stranded RNA that can induce the degradation of the target mRNA or inhibit the expression of the target gene via cleavage of the target mRNA.

The siRNAs according to the present invention, which bind to a nucleotide sequence corresponding to positions 777 to 795 of rpS3 mRNA and a nucleotide sequence corresponding to positions 796 to 814 of rpS3 mRNA, are represented by SEQ ID NOS: 2 and 3, respectively.

The siRNAs of the present invention are not limited to the completely paired one, and may contain nonpairing portions due to mismatch (the corresponding nucleotides are not complementary), bulge (lacking in the corresponding complementary nucleotide on one strand), and the like.

The siRNAs of the present invention may be a double-stranded RNA comprising 10-40 nucleotides, preferably 15-30 nucleotides, more preferably 19-21 nucleotides, which can interfere with the activity and expression of rpS3.

As used herein, the term "length of the siRNA" refers to the number of nucleotides that form a double strand (pairing). The terminal structure of the siRNA of the present invention may be either blunt or cohesive, as long as the siRNA can silence, reduce, or inhibit the target gene expression due to its RNAi effect.

The cohesive end structure may be the 3'-end overhang structure and the 5'-end overhanging structure. The number of overhanging nucleotides is not specifically limited, but may be, for example, 1-8 nucleotides, preferably 1-4 nucleotides. In addition, the overhang on one end of the siRNA may comprise dTdT, UU, or a sequence identical or complementary to rpS3 mRNA following the double-strand forming portion. In addition, the terminal structure of the siRNA is not necessarily to have the cut off structure at both ends, and may have a stem-loop structure in which ends of one side of double-stranded RNA are connected by a linker RNA. Furthermore, there is no particular limitation in the length of the linker as long as it has a length so as not to hinder the pairing of the stem portion.

In order to prevent rapid in vivo degradation caused by nucleases and enhance in vivo stability, the siRNA of the present invention can be chemically modified by a general method known in the art. For example, the hydroxyl group at 2'position of sugar (ribose ring) of at least one nucleotide in the siRNA may be substituted with hydrogen, halogen, —O-alkyl, —O-acyl or an amino group, specifically H, OR, R, R'OR, SH, SR, $NH_2$, NHR, $NR_2$, $N_3$, CN, F, Cl, Br, I, etc., wherein R may be alkyl or aryl, preferably an alkyl group having 1 to 6 carbon atoms, and R' may be alkylene, preferably an alkylene group having 1 to 6 carbon atoms. Alternatively, the phosphate backbone constituting the nucleotide may be modified with, for example, phosphorothioate, phosphorodithioate, alkyl phosphonate or phosphoroamidate.

In the chemical modification, at least one nucleotide in the siRNA of the present invention may be substituted so that it will be present as any one nucleic acid analogue selected from among LNA (locked nucleic acid), UNA (unlocked nucleic acid), morpholino, and PNA (peptide nucleic acid). The preparation of LNA, UNA, PNA, morpholino and the like can be performed according to the knowledge known in the art based on the siRNA sequence information provided in the present invention and can be performed with reference to previous literature (Veedu R N, Wengel J., *Chem Biodivers*, 7(3):536-42, 2010; Demidov V V., *Trends Biotechnol*, 21(1):4-7, 2003; Shantanu Karkare et al., *Appl Microbiol Biotechnol*, 71:575-586, 2006).

In an example of the chemical modification of the siRNA, the phosphodiester bond of the siRNA sense or antisense strand may be substituted with boranophosphate or phosphorothioate to increase the nuclease resistance of the siRNA. For example, the substitution may be introduced into the 3' or 5' end or both ends of the siRNA sense or antisense strand, preferably the RNA terminus, for example, the 3' end overhang (for example, (dT)n, n=an integer ranging from 1 to 5, preferably from 2 to 4).

As another example, ENA (ethylene bridge nucleic acid) or LNA (locked nucleic acid) may be introduced into the 5' or 3' end or both ends of the siRNA sense or antisense strand. Preferably, it may be introduced into the 5' end of the siRNA sense strand. In this case, the siRNA stability can be increased without influencing the RNAi activity, and the immune response and non-specific inhibitory effect of the siRNA can be reduced.

The siRNAs of the present invention may include variants having at least one substitution, insertion, deletion or combinations thereof, which are functional equivalents with a variation that does not reduce the activity thereof. For example, the siRNA of the present invention may include those showing a homology of at least 80%, preferably at least 90%, and more preferably at least 95%, to the nucleotide sequence thereof. This homology can be easily determined by comparing the nucleotide sequence with the corresponding part of the target gene using a computer algorithm widely known in the art, for example, the Align or BLAST algorithm.

The siRNA of the present invention may be in a complete form in which two RNA strands are paired to form a double strand, that is, a form in which siRNA is directly synthesized in vitro and introduced into cells by transfection. Alternatively, it may be in a modified form that has a short hairpin structure so that it can be used in transfection by a plasmid-based shRNA vector and a PCR-induced siRNA expression cassette.

The siRNA can be synthesized by various methods known in the art, including a direct chemical synthesis method (Sui G et al., Proc Natl Acad Sci USA, 99:5515-5520, 2002), a synthesis method based on in vitro transcription (Brummelkamp T R et al., Science, 296:550-553, 2002), and a method in which a long double-stranded RNA synthesized by in vitro transcription is cleaved by an RNaseIII family enzyme (Paul C P et al., Nature Biotechnology, 20:505-508, 2002).

Figure 2:
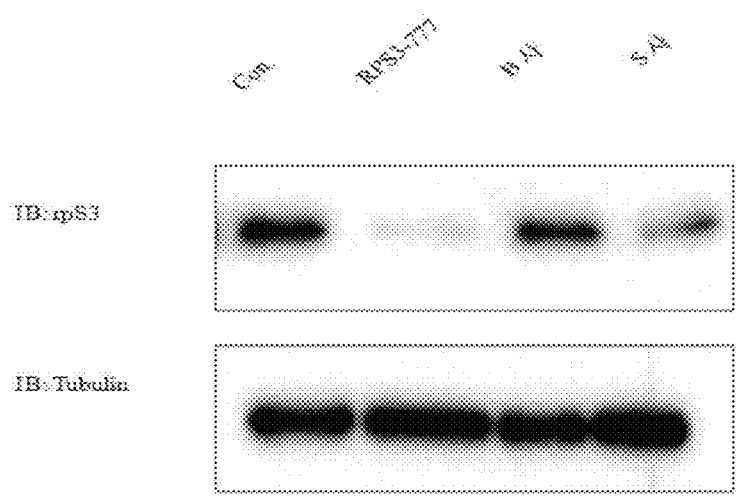
FIG. 2 shows the results of comparing the efficiency of an rpS3 siRNA (lane1: control, lane 2: RPS3-777, lane 3: B company, and lane 4: S company).

In the present invention, in order to examine the difference of the siRNA of the present invention from a commercially available siRNA in terms of efficiency, the same amounts of the siRNAs were introduced into mouse fibroblasts, and the levels of rpS3 in the cells were measured by Western blotting. As a result, it was found that the change in the level of the rpS3 protein was very significant. Specifically, the siRNA of company B showed low efficiency, whereas the product of company S reduced the level of the protein by about 50-60%, but the siRNA of the present invention had the effect of knocking down about 80-90% of the rpS3 protein (FIG. 2).

The siRNAs according to the present invention can be easily used in human, mouse and monkey cells.

In an example of the present invention, in order to construct an siRNA system that regulates only endogenous rpS3 protein in cells and does not influence exogenous overexpressed rpS3 protein, a Flag-tagged rpS3 construct (DNA) was introduced into HT1080 cells, after which the cells were treated with G418 (800 ug/ml) to screen only cells introduced with the DNA, thereby obtaining single cells.

Figure 3:
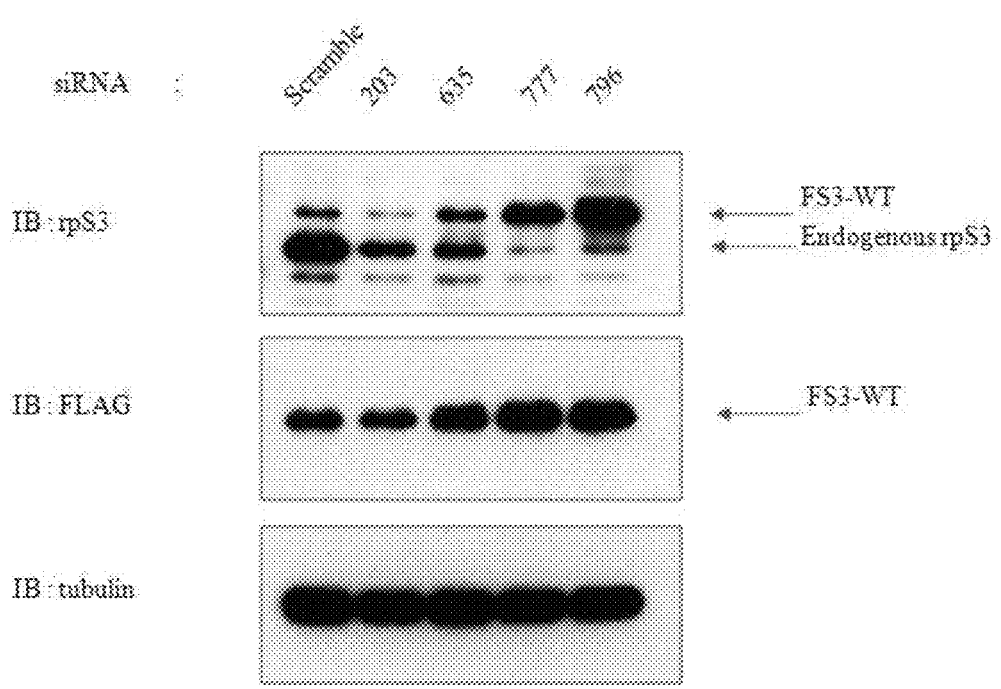
FIG. 3 shows the results of identifying a stable cell that expresses rpS3 which is not influenced by siRNA (lane 1: scramble siRNA, lane 2: RPS3-203, lane 3: RPS3-635, lane 4: RPS3-777, and lane 5: RPS3-796).

In order to examine the effect of the siRNA in the cells and the expression of the tagged protein in the cells, the cells were treated with each of a scramble siRNA and RPS3-77 and 796 siRNAs, and the levels of rpS3 protein and Flag-rpS3 protein were measured by Western blotting. As a result, it was shown that the control scramble siRNA had no effect, and the RPS3-777 and 796 inhibited the level of endogenous rpS3, but the level of the Flag-tagged rpS3 protein increased rather than decreased (FIG. 3).

Based on such results, it can be seen that the expression level of the Flag-rpS3 protein securely increases, and thus the expression level thereof in not only a wild-type but also a mutant-type can increase. Thus, a system enabling to study the biological function of this protein can be constructed.

Therefore, the siRNAs according to the present invention are characterized in that they inhibit the expression of endogenous rpS3 protein without influencing tagged overexpressed protein.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1

Investigation of Target Sequence for siRNA

In order to find the site targeted by siRNA, sequences were substituted into a program that searches for a sequence targeting the DNA sequence of rpS3, and the results were comparatively analyzed (Ambion, Promega, OligoEngine, Dharmacon).

The rpS3 DNA sequence was divided into three portions: a portion that is synthesized into the protein; the 5'-UTR portion; and the 3'-UTR portion. A plasmid constructed for overexpression of the rpS3 protein was composed only of the portion for forming the protein. In addition, a program that searches for a target sequence having high siRNA efficiency from the 3'-UTR including untranslated exon-7 was used (Ambion, Promega, Dharmacon). Furthermore, human and mouse DNA sequences were substituted into the program to search for a target sequence showing high efficiency in both the human and mouse DNAs.

Among the predicted sequences capable of exhibiting high effects upon targeting, the portion presented commonly by the programs was determined as the siRNA target sequence. The siRNA of the determined sequence was synthesized by Dharmacon. The control siRNA used was AccuTarget™ Negative control siRNA manufactured by Bioneer (Korea).

siRPS3-777 (RPS3-777, siRNA777, or 777) was synthesized so as to target a sequence consisting of the nucleotides at positions 777-795 of rpS3 mRNA, and siRPS3-796 (RPS3-796, siRNA796, or 796) was synthesized so as to target a sequence consisting of the nucleotides at positions 796-814 of rpS3 mRNA (Table 1).

TABLE 1

Nucleotide sequences and lengths of siRNAs for rpS3

| siRNA oligo | siRNA sequence | | Sequence lengths |
|---|---|---|---|
| siRPS3-777 | CAG CTG TAT TCT GGA GTC T | SEQ ID NO: 2 | 19 Mer |
| siRPS3-796 | GGA TGT TGC TCT CTA AAG A | SEQ ID NO: 3 | 19 Mer |

Example 2

Regulation of rpS3 Expression Level in Cells by siRNA

In order to examine whether the constructed rpS3 siRNA efficiently operates after intracellular introduction, an experiment was performed using various mammalian cells. Specifically, each of the siRNAs (200 pmole) was introduced into cells by reverse transfection using 8 μl of Lipofectamine RNAiMAX (Invitrogen). Herein, the animal cells were added to 60 mm dishes at a density of about 20,000 cells per dish. At 16 hours after transfection, the cells were harvested, and the level of rpS3 protein in the cells was analyzed by Western blotting.

Each of a scramble siRNA as a control, RPS3-203 (203) and 635 (635) constructed previously by the present inventors so as to target the rpS3 protein, and siRPS3-777 and 796 constructed in this Example, was introduced into HeLa (KCLB 10002) and 293T (KCLB 21573) animal cells.

As a result, as can be seen in FIG. 1, the scramble siRNA used as the control showed no change in the level of the rpS3 protein in the cells, whereas RPS3-777 and 796 according to the present invention greatly inhibited the expression level of the rpS3 protein compared to RPS3-203 and 635 that have been used in the prior art.

Example 3

Comparison with Commercially Available siRNA (Mouse)

siRNAs for many proteins are commercially available from various companies. Among them, siRNAs targeting not only human rpS3 protein, but also mouse rpS3 protein in mouse cell lines that are frequently used in experiments, are also commercially available from reagent companies. In this Example, in order to examine the difference of the siRNA (siRPS3-777) of Example 1 from commercially available siRNA in terms of efficiency, the sample amounts (200 pmole) of the siRNAs were introduced into mouse fibroblast cells, and the efficiencies thereof were compared.

As a result, as can be seen in FIG. 2, the siRNA of company B generally showed low efficiency, whereas the product of company S inhibited about 50-60% of the protein, but the siRNA (RPS3-777) of the present invention showed the effect of knocking down about 80-90% of the rpS3 protein.

Example 4

Construction of Cells Constitutively Expressing siRNA-Resistant rpS3

In actual experiments, the comparison of a wild-type (WT) protein with a mutant protein obtained by changing the function of the wild-type protein is very important. Thus, in this Example, a tagging system was used for the comparison between the two proteins, and the overexpression of the proteins was induced. However, even when the proteins are overexpressed, accurate analysis of the proteins is difficult due to endogenous protein. For this reason, in this Example, it was attempted to construct an siRNA system that does not penetrate a tagged protein.

Specifically, in order to make rpS3-overexpressing cells, a Flag-tagged rpS3 construct (DNA) was introduced into HT1080 cells, after which the cells were treated with G418 (800 ug/ml) to select only cells introduced with the DNA, thereby obtaining single cells. The obtained cells have the property of constitutively expressing a specific protein, and thus are referred to as "stable cells". In order to examine the effect of the siRNA in the cells and the expression level of the tagged protein in the cells, the cells were treated with each of a scramble siRNA, or RPS3-777 and 796 siRNAs.

As a result, as can be seen in FIG. 3, the results of treatment with the siRNAs indicated that the control scramble had no effect on the expression of the protein, and the conventional siRNA and the siRNA of the present invention all reduced the expression of endogenous rpS3 in the wild-type cell line. However, the level of the Flag-tagged rpS3 protein was reduced by 203 (RPS3-203) and 635 (RPS3-635), but was rather increased by 777 (RPS3-777) and 796 (RPS3-796). This suggests that Flag-rpS3 that is constitutively expressed is quantitatively regulated together with endogenous rpS3. Thus, it can be seen that the expression level of the Flag-rpS3 protein securely increases, and thus the expression level thereof in not only a wild-type but also a mutant-type can increase. Thus, a system enabling to study the biological function of this protein was constructed. The present invention can also applied to proteins other than the rpS3 protein, and the results obtained using the siRNA can be confirmed again by the method as described in this Example. Thus, there is an advantage in that the off-target effect becoming the biggest problem in experiments employing siRNA can be eliminated.

INDUSTRIAL APPLICABILITY

As described above, the siRNA according to the present invention specifically inhibits the expression of endogenous rpS3 protein in cells without influencing tagged overexpressed protein. It has an excellent inhibitory effect on the expression of rpS3 compared to conventional commercially available products, and thus is excellent in terms of economy and efficiency.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for inhibiting the expression of rpS3 protein, the method comprising binding an siRNA to an rpS3 mRNA, wherein the siRNA is represented by SEQ ID NO: 2 or SEQ ID NO: 3, and wherein the siRNA inhibits the expression of the rpS3 protein.

2. The method of claim 1, wherein the siRNA has a length of 15-21 nucleotides.

3. The method of claim 1, wherein the siRNA of SEQ ID NO: 2 binds to a nucleotide sequence corresponding to positions 777 to 795 of rpS3 mRNA.

4. The method of claim 1, wherein the siRNA of SEQ ID NO: 3 binds to a nucleotide sequence corresponding to positions 796 to 814 of rpS3 mRNA.

5. The method of claim 1, wherein the rpS3 mRNA has a nucleotide sequence of SEQ ID NO: 1.

* * * * *

SEQUENCE LISTING

```
<160> NUMBER OF SEQ ID NOS: 3

<210> SEQ ID NO 1
<211> LENGTH: 855
<212> TYPE: DNA
<213> ORGANISM: Artificial Sequence
<220> FEATURE:
<223> OTHER INFORMATION: Synthesized human nucleotide sequence for
      expression of rpS3

<400> SEQUENCE: 1
cctttccttt cagcggagcg cggcggcaag atggcagtgc aaatatccaa gaagaggaag    60
```

```
tttgtcgctg atggcatctt caaagctgaa ctgaatgagt ttcttactcg ggagctggct    120
gaagatggct actctggagt tgaggtgcga gttacaccaa ccaggacaga aatcattatc    180
ttagccacca gaacacagaa tgttcttggt gagaagggcc ggcggattcg ggaactgact    240
gctgtagttc agaagaggtt tggctttcca gagggcagtg tagagcttta tgctgaaaag    300
gtggccacta gaggtctgtg tgccattgcc caggcagagt ctctgcgtta caaactccta    360
ggagggcttg ctgtgcggag ggcctgctat ggtgtgctgc ggttcatcat ggagagtggg    420
gccaaaggct gcgaggttgt ggtgtctggg aaactccgag gacagagggc taaatccatg    480
aagtttgtgg atggcctgat gatccacagc ggagaccctg ttaactacta cgttgacact    540
gctgtgcgcc acgtgttgct cagacagggt gtgctgggca tcaaggtgaa gatcatgctg    600
ccctgggacc caactggtaa gattggccct aagaagcccc tgcctgacca cgtgagcatt    660
gtggaaccca aagatgagat actgcccacc acccccatct cagaacagaa gggtgggaag    720
ccagagccgc ctgccatgcc ccagccagtc cccacagcat aacagggtct ccttggcagc    780
tgtattctgg agtctggatg ttgctctcta aagacccttta ataaattttt gtacaaagac    840
aaaaaaaaaa aaaaa                                                    855

<210> SEQ ID NO 2
<211> LENGTH: 19
<212> TYPE: DNA
<213> ORGANISM: Artificial Sequence
<220> FEATURE:
<223> OTHER INFORMATION: Synthesized nucleotide sequence siRPS3-777 for
      inhibiting expression of rpS3

<400> SEQUENCE: 2
cagctgtatt ctggagtct                                                 19

<210> SEQ ID NO 3
<211> LENGTH: 19
<212> TYPE: DNA
<213> ORGANISM: Artificial Sequence
<220> FEATURE:
<223> OTHER INFORMATION: Synthesized nucleotide sequence siRPS3-796 for
      inhibiting expression of rpS3

<400> SEQUENCE: 3
ggatgttgct ctctaaaga                                                 19
```